(12) United States Patent
Hedenberg

(10) Patent No.: US 6,263,873 B1
(45) Date of Patent: Jul. 24, 2001

(54) BELLOWS ARRANGEMENT FOR A VENTILATOR/ANESTHESIA SYSTEM

(75) Inventor: Håkan Hedenberg, Järfälla (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/243,543

(22) Filed: Feb. 3, 1999

(30) Foreign Application Priority Data

Feb. 25, 1998 (SE) .................................... 9800561

(51) Int. Cl.⁷ .................................................. A61M 16/00
(52) U.S. Cl. ................................ 128/204.28; 128/205.13; 128/205.18; 128/204.18; 128/203.12; 128/203.28
(58) Field of Search ...................... 128/202.29, 203.12, 128/203.28, 204.18, 204.28, 205.13, 205.17

(56) References Cited

U.S. PATENT DOCUMENTS

| | | |
|---|---|---|
| 5,678,540 | 10/1997 | Kock et al. . |
| 5,683,232 * | 11/1997 | Adahan ........................... 128/205.24 |
| 6,123,072 * | 9/2000 | Downs ............................ 128/204.21 |

FOREIGN PATENT DOCUMENTS

| | | |
|---|---|---|
| 0 557 134 | 8/1993 | (EP) . |
| 466 635 | 3/1992 | (SE) . |
| WO 97/01367 | 1/1997 | (WO) . |

\* cited by examiner

*Primary Examiner*—Glenn K. Dawson
(74) *Attorney, Agent, or Firm*—Schiff Hardin & Waite

(57) ABSTRACT

A bellows arrangement for a ventilator/anesthesia system has a rigid container in which a bellows is arranged. The first end of the bellows is fastened to one end of the container, and the other end is displaceable relative to the first end. The container is connected to a propellant source of the ventilator/anesthesia system, and the bellows is in gaseous communication with a respiratory circuit of the ventilator/anesthesia system at the first end. In order to insure that the bellows always moves smoothly in a simple and inexpensive fashion, the second end of the bellows is provided with a guidance fixture which is connected to the container in every position of the second end so that, in an expansion or compression of the bellows, the second end is always displaced along the center axis while remaining substantially of the bellows parallel to the first end.

9 Claims, 3 Drawing Sheets

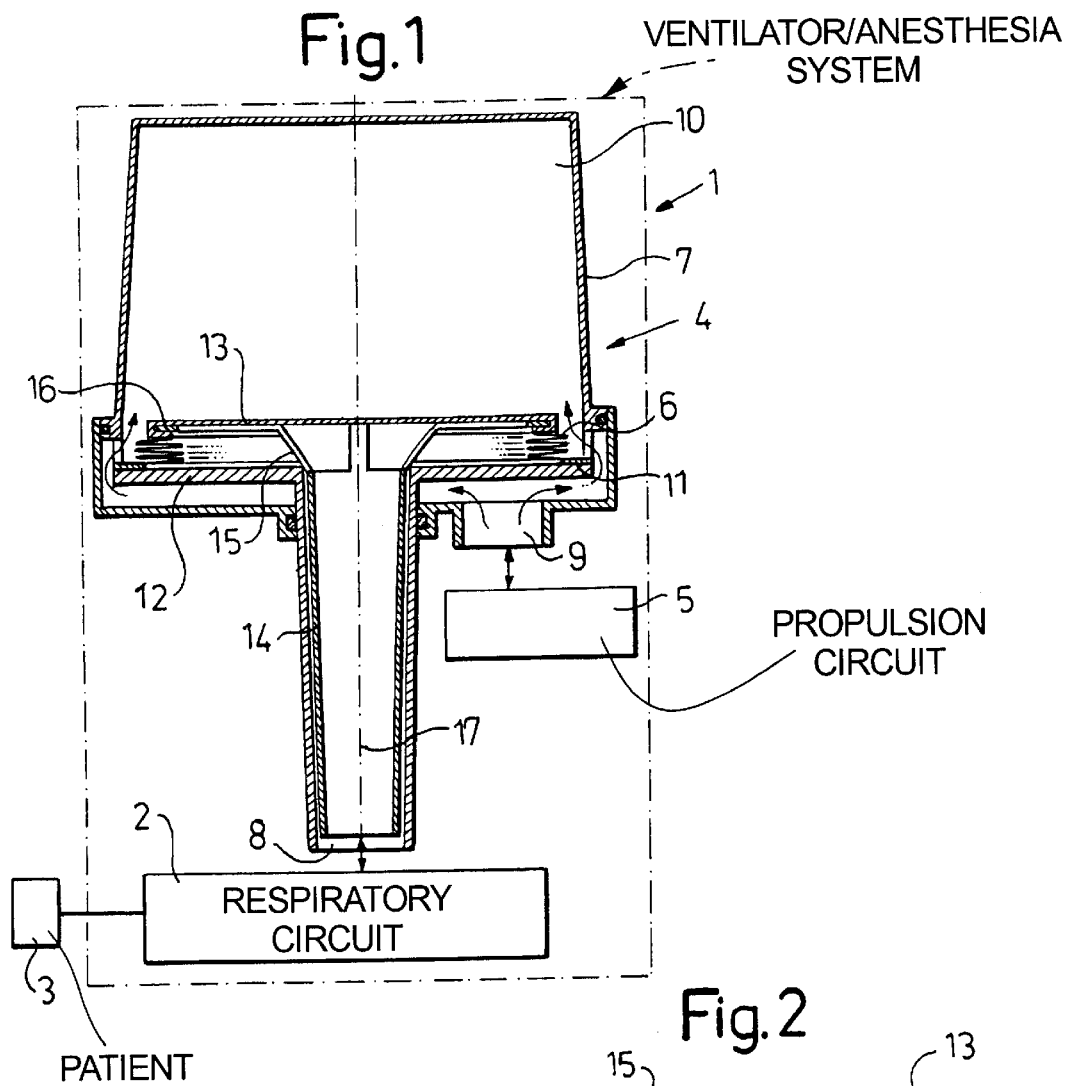
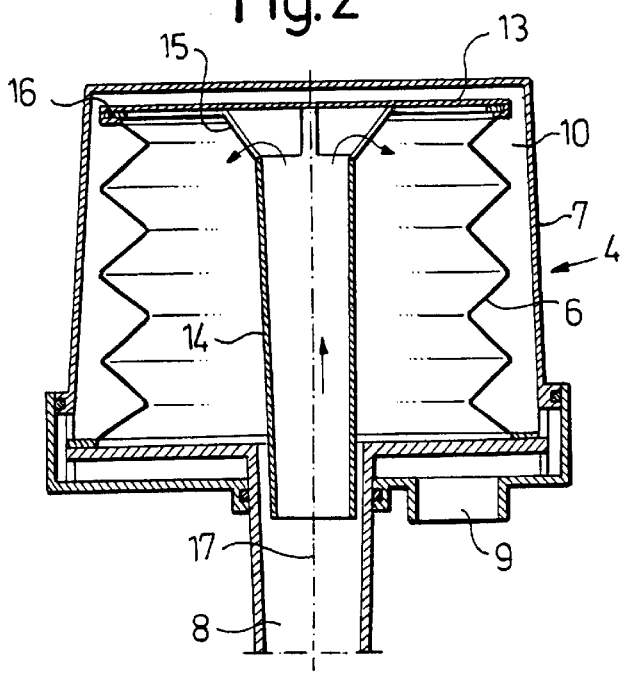

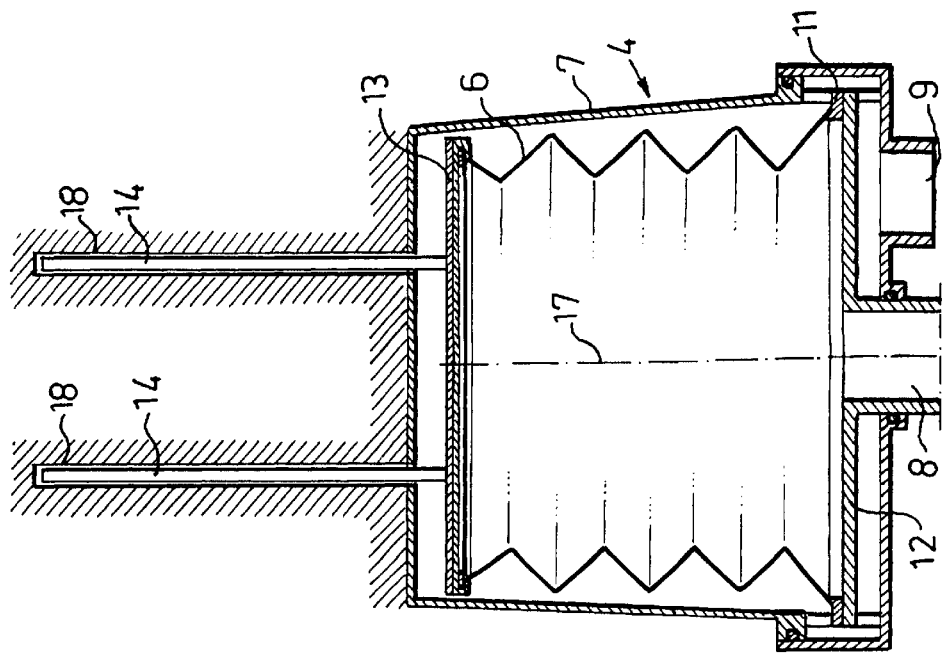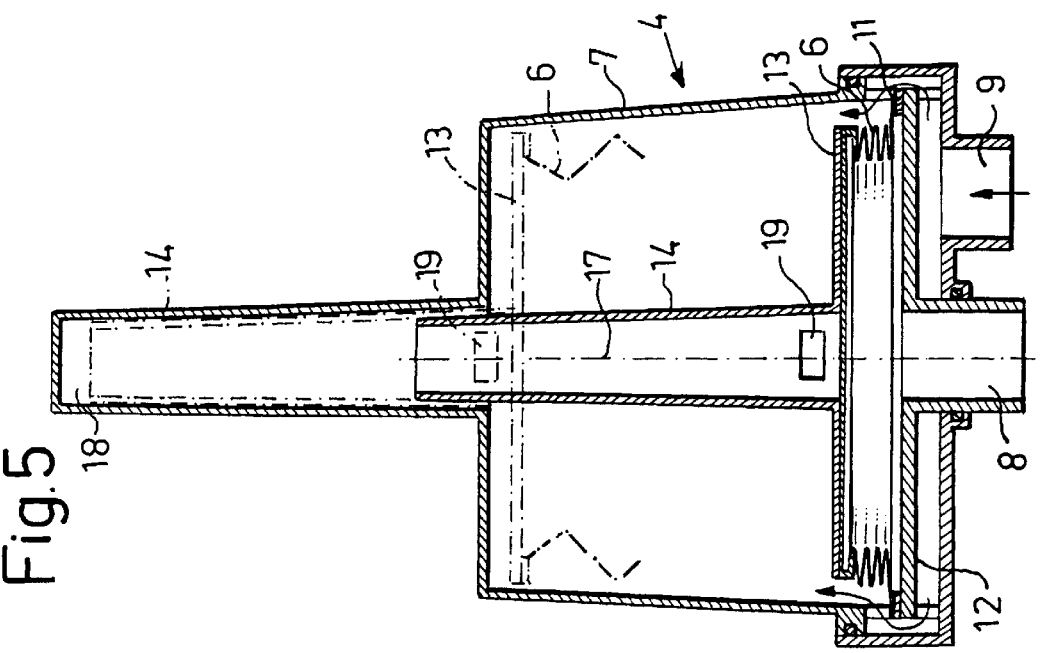

BELLOWS ARRANGEMENT FOR A VENTILATOR/ANESTHESIA SYSTEM

BACKGROUND OF THE INVENTION

1. Field of the Invention

The present invention relates to a bellows arrangement for a ventilator/anesthesia system of the type wherein the bellows arrangement has a rigid container in which a bellows is arranged, with a first end of the bellows fastened to one end of the container, and the second end being displaceable relative to the first end, and wherein the container can be attached to a propellant source and the bellows can be connected to a respiratory circuit at the aforementioned first end.

2. Description of the Prior Art

An anesthesia system with a bellows arrangement of the aforementioned type is illustrated and described in U.S. Pat. No. 5,678,540. The anesthesia system includes a respiratory circuit which can be connected to a patient, the aforementioned bellows arrangement, and a propellant source for controlling the flow of respiratory gas in the respiratory circuit. The interior of the bellows is connected to the respiratory circuit, as described above, and the space between the bellows and the wall of the container is connected to a propellant source.

For the initiation of an inhalation phase, the propellant source feeds a propellant to the space between the bellows and the container. When the pressure in this space is higher than the pressure in the bellows, the bellows begins to be compressed, causing respiratory gas to be fed to the patient. An exhalation phase follows an inhalation phase. During an exhalation phase, the propellant is released from the space between the bellows and the container, causing a relative pressure excess in the respiratory circuit and in the bellows to arise. The bellows then starts to expand, allowing the respiratory gas to flow out of the patient's lungs. This is repeated for each breathing cycle. Similar systems with bellows arrangements of this type are illustrated and described in published Swedish Application 466 635 and in European Application 0 557 134. Since the container is usually transparent, the movement sequence of the bellows is visible to the environment. In an expansion, or a compression, the bellows can wobble and/or its free end can end up in an oblique position, which does not affect the function, though it can disturb the hospital personnel.

SUMMARY OF THE INVENTION

It is an object of the present invention to provide a bellows arrangement of the type initially described wherein it is guaranteed, in a simple and inexpensive manner, that the bellows always moves smoothly.

This object is achieved in a bellows arrangement of the type initially described wherein a second end of the bellows is provided with at least one guidance fixture which is disposed in the container in every position of the second end to insure that, during an expansion or a compression of the bellows, the second end is always displaced along the center axis of the bellows in parallel fashion. The movements of the second end in the axial direction are stabilized by the guidance fixture, and so a wobbling of the bellows or an oblique position of the free end can not occur.

In one embodiment of the inventive bellows arrangement the connection to the respiratory circuit is tubular and is a part of the container, and the guidance fixture is an elongated part which is attached to the second end and is directed toward the first end. This elongated part has a length, diameter and placement so that, in all positions of the bellows, it is disposed in the tubular part of the connection such that it can be frictionlessly displaced therein, and the elongated part is constructed such that it allows gas to pass through the connection in the filling or evacuating of the bellows. Utilization of the already existing connection for the respiratory circuit results in an extremely simple construction for the bellows guidance, while at the same time a compact bellows arrangement is obtained by the direction and position of the guidance fixture.

The guidance fixture can inventively be a tubular part, but preferably is a part with a stellate cross-section. It is essential that the guidance fixture be constructed such that it allows gas to pass through the connection in the filling of the bellows or in the evacuation of the bellows.

In a further embodiment of the inventive bellows arrangement, the guidance fixture is at least one elongated part which is attached to the second end of the bellows and is directed away from the first end, and the container has a recess of a shape and placement so that, in all positions of the bellows, the elongated part is disposed in the recess such that it can be frictionlessly displaced therein.

In this further exemplary embodiment, the guidance fixture also can be a tubular part or a part with a stellate cross-section. The guidance element can alternatively be a rod or peg.

Additional stabilizing of the movements of the bellows in the axial direction is achieved in an embodiment wherein the second side is provided with two or more guidance fixture with corresponding recesses in the container.

DESCRIPTION OF THE DRAWINGS

FIG. 1 schematically illustrates an anesthesia system containing a first embodiment of an inventive bellows arrangement, with the bellows in compressed position.

FIG. 2 shows the bellows arrangement according to FIG. 1 with the bellows in an expanded position.

FIG. 5 schematically illustrates a second embodiment of an inventive bellows arrangement.

FIG. 6 schematically illustrates a further version of the second embodiment.

DESCRIPTION OF THE PREFERRED EMBODIMENTS

Figure 3:
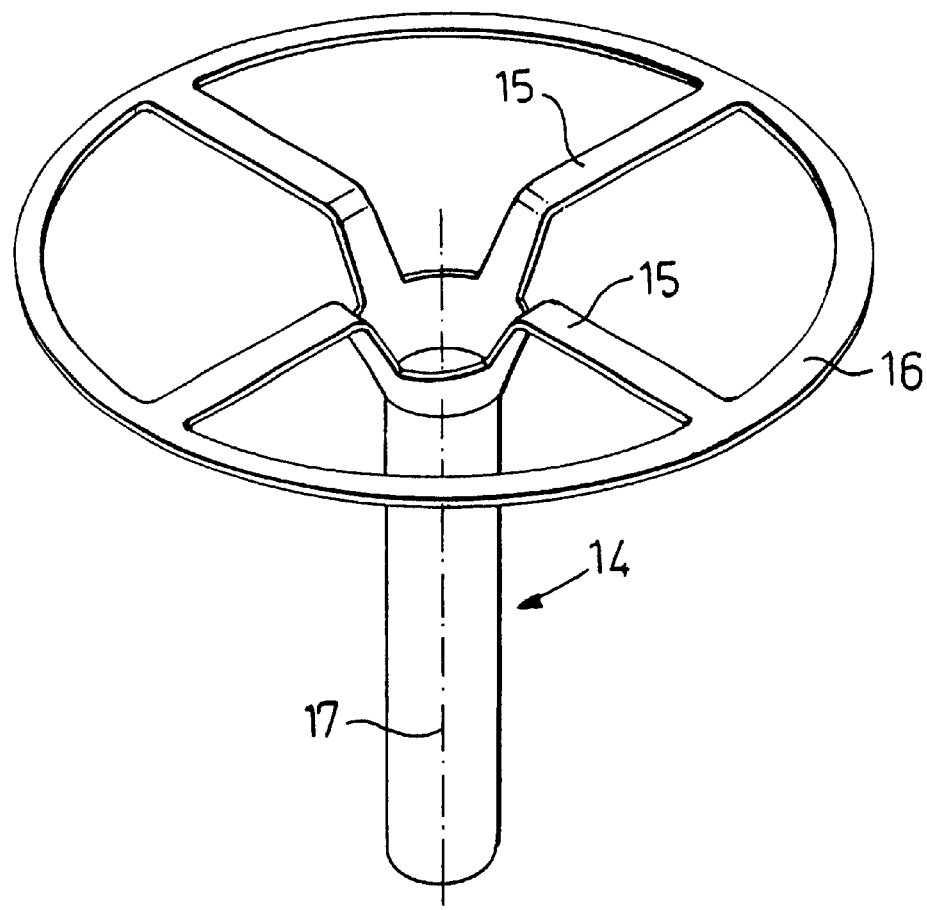
FIG. 3 is a perspective view of the guidance fixture for the bellows in the embodiment according to FIG. 1 and 2.

FIG. 1 schematically depicts an anesthesia system 1 having a respiratory circuit 2 for connection to a patient 3, an inventive pressure-exchanging bellows arrangement 4, and a propulsion circuit 5 for controlling a respiratory gas flow in the respiratory circuit 2. U.S. Pat. No. 5,678,540 teaches a basic anesthesia system of a similar type(but with a different bellows arrangement). The pressure-exchanging bellows arrangement 4, which is detailed below, includes a bellows 6, which is arranged in a rigid, transparent container 7 (known as "bag and bottle"), the interior of the bellows 6 being connected to the respiratory circuit 2 via a connection 8, and the space 10 between the bellows 6 and the walls of the container 7 being connected to the propulsion circuit 5 via a connection 9. If an inhalation phase is to be initiated, the propulsion circuit 5 feeds a propellant from a propellant source therein to the space 10 between the bellows 6 and the container 7. When the pressure in this space 10 becomes higher than the pressure in the bellows 6, the bellows 6 starts to become compressed, causing respiratory gas to be fed to the patient. The arrows in FIG. 1 indicate the path into the space 10. A compressed bellows 6 is depicted in this FIG. 1.

An exhalation phase follows an inhalation phase. During the exhalation phase, the propellant is released from the space 10 between the bellows 6 and the container 7, and a relative pressure excess arises in the respiratory circuit 2 and in the bellows 6. The bellows 6 then starts to expand, allowing respiratory gas from the lungs of the patient 3 to flow into the bellows 6 via the connection 8. An expanded bellows 6 is depicted in FIG. 2. This is repeated as described for each respiratory cycle.

FIG. 1 and FIG. 2 show that the first end 11 of the bellows 6 is fastened to a plate 12. The other end 13 of the bellows 6 is provided with a guidance fixture 14, which in the exemplary embodiment is a tubular part that is directed toward the end 11. The tubular part has a length, diameter and placement such that, in all positions of the bellows 6, it is disposed in the connection 8, which is also a tubular, so that the guidance fixture 14 can be frictionlessly displaced in the connection 8. The guidance fixture 14 is constructed so that, in the filling or evacuation of the bellows 6, it allows the gas to pass through the connection 8. The arrows in FIG. 2 indicate the path of the gas into the bellows 6. Due to the guidance fixture 14, the end 13 can always be displaced along the center axis 17 of the bellows 6 in an expansion or compression of the bellows 6 while remaining substantially parallel to the plate 12. The bellows 6 thus exhibits a regular pattern of movement without the danger of the bellows 6 tilting or wobbling.

FIG. 3 depicts the guidance fixture 14 separately in a perspective view. The guidance fixture 14 includes the aforementioned elongated tubular part, which is connected to a collar 16 via band-like spacers 15. The collar 16, which is also depicted in FIGS. 1 and 2, is connected to the end 13 of the bellows 6. Openings through which the gas can pass are formed between the end 13 and the elongated part of the guidance fixture 14 by the structure of the spacers 15.

Figure 4:
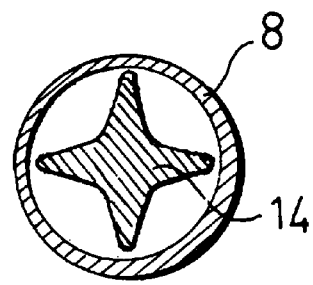
FIG. 4 is a cross-section of a guidance fixture for the bellows, in a further version having a form that differs from the form depicted in FIG. 3.

FIG. 4 depicts a cross-section of another version of the guidance fixture 14. Gas can pass in the spaces between any adjacent pair of the projecting ribs of the guidance fixture 14 and the inner wall of the connection 8 as a result of the stellate cross-section of this version of the guidance fixture 14. The elongated part of the guidance fixture 14 thus can be fastened directly to the end 13 of the bellows 6 without the need for a collar.

FIG. 5 depicts a bellows arrangement 4 which differs from that described in connection with the FIGS. 1 and 2 only in that the guidance fixture 14 which is attached to the end 13 of the bellows 6 is directed in the opposite direction from the end 11. In this bellows arrangement, the container 7 is provided with a recess 18 having a placement and form so that, in all positions of the bellows 6, the guidance fixture 14 is disposed therein such that it can be frictionlessly displaced. FIG. 5 depicts the bellows 6 in both a compressed position in solid lines and in an expanded position with dashed lines. To prevent an excess pressure from arising in the recess 18 when the guidance fixture 14 is pushed into the recess 18 in an expansion of the bellows, the guidance fixture 14 is provided with a hole 19.

FIG. 6 shows that the bellows 6 can be provided with a guidance fixture 14 having two or more elements, which can be respectively displaced in corresponding recesses 18. In this exemplary embodiment in FIG. 6, two elements in the form of rods or pegs 18 are used. Such an embodiment can give additional stability in connection with the movements of the bellows 6 along the center axis 17.

In the embodiment of the invention wherein the guidance fixture 14 directed toward the first end 11, the tubular part of the guidance fixture 14 can be arranged in a recess at this end 11 of the container 7 such that it can be frictionlessly displaced. In such an exemplary embodiment, the connection 8 of the bellows 6 is not used as the part in which the tubular part is displaced. Moreover, the guidance fixture 14 can have other forms in the context of the invention besides those which are described and illustrated herein. The basic function which must be performed is that the bellows is always guided so as to be displaced along the center axis of the bellows with its movable end moving in parallel fashion.

Although modifications and changes may be suggested by those skilled in the art, it is the intention of the inventor to embody within the patent warranted hereon all changes and modifications as reasonably and properly come within the scope of his contribution to the art.

I claim as my invention:

1. A bellows arrangement for a ventilator/anesthesia system, said ventilator/anesthesia system having a propellant source and a respiratory circuit, said bellows arrangement comprising:

a rigid container having an interior;

a bellows disposed in said rigid container, said bellows having an interior and an exterior and a first end and a second end disposed opposite to and substantially parallel to each other, said first end being stationarily mounted in said rigid container and said second end being movable in said rigid container relative to said first end, said bellows having a center axis;

said container having a connection for placing said interior of said container and said exterior of said bellows in gaseous communication with said propellant source for allowing compression and expansion of said bellows in said rigid container;

said bellows having a connection for placing said interior of said bellows in gaseous communication with said respiratory circuit; and a guidance fixture at said second end of said bellows and disposed in said container at every position of said second end of said bellows as said second end moves relative to said first end during expansion and compression of said bellows, said guidance fixture guiding said second end of said bellows so that said second end always moves along said center axis of said bellows while remaining substantially parallel to said first end.

2. A bellows arrangement as claimed in claim 1 wherein said connection to said respiratory circuit is tubular and is a part of said container disposed adjacent to said first end of said bellows, and wherein said guidance fixture comprises an elongated part mounted at said second end of said bellows and projecting through said interior of said bellows toward said first end, said elongated part having a length and a diameter so that as said second end of said bellows moves relative to said first end said elongated part is frictionlessly displaced in said connection to said respiratory circuit, and wherein said elongated part has at least one pathway therein allowing gas to flow through said connection to said respiratory circuit to said interior of said bellows during compression and expansion of said bellows.

3. A bellows arrangement as claimed in claim 2 wherein said guidance fixture comprises a tubular fixture having an interior, and an attachment structure, having at least one opening therein, attaching said tubular fixture to said second end of said bellows, said pathway comprising said interior of said tubular fixture and said at least one opening in said attachment structure.

4. A bellows arrangement as claimed in claim 3 wherein said attachment structure comprises a plurality of spaced bands connecting one end of said tubular fixture to said second end of said bellows.

5. A bellows arrangement as claimed in claim 2 wherein said guidance fixture has a stellate cross-section having a plurality of projecting, spaced apart ribs, and wherein said pathway comprises at least one space between any adjacent pair of said plurality of ribs.

6. A bellows arrangement as claimed in claim 1 wherein said guidance fixture is attached to said second end of said bellows and projects from said exterior of said bellows away from said first end of said bellows, and wherein said container comprises at least one recess disposed at said container adjacent to said second end of said bellows, said recess receiving said guidance fixture as said second end of said bellows moves relative to said first end during expansion and compression of said bellows.

7. A bellows arrangement as claimed in claim 6 wherein said guidance fixture comprises a tubular fixture.

8. A bellows arrangement as claimed in claim 7 wherein said tubular fixture has an interior and a first end attached to said second end of said bellows and an open second end, and wherein said tubular fixture has at least one opening therein communicating said interior of said container with said interior of said tubular fixture.

9. A bellows arrangement as claimed in claim 6 wherein said guidance fixture comprises at least one rod received in and displaceable in said recess of said container.

* * * * *